(12) United States Patent
Gillis et al.

(10) Patent No.: US 7,282,038 B2
(45) Date of Patent: Oct. 16, 2007

(54) COMPRESSION APPARATUS

(75) Inventors: Heather Gillis, Sharon, MA (US); Kristin Watson, North Attleboro, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 263 days.

(21) Appl. No.: 10/784,604

(22) Filed: Feb. 23, 2004

(65) Prior Publication Data

US 2005/0187499 A1    Aug. 25, 2005

(51) Int. Cl.
*A61H 9/00* (2006.01)
(52) U.S. Cl. .................. 601/151; 601/148; 602/13
(58) Field of Classification Search ............... 601/148, 601/149, 150–152; 602/13, 23, 27, 60–62, 602/65; 606/202; 128/882, DIG. 20
See application file for complete search history.

(56) References Cited

U.S. PATENT DOCUMENTS

| | | |
|---|---|---|
| 1,608,239 A | 11/1926 | Rosett |
| 2,694,395 A | 11/1954 | Brown |
| 3,164,152 A | 1/1965 | Nicoll |
| 3,245,405 A | 4/1966 | Gardner |
| 3,454,010 A | 7/1969 | Lilligren et al. |
| 3,561,435 A | 2/1971 | Nicholson |
| 3,728,875 A | 4/1973 | Hartigan et al. |
| 3,786,805 A | 1/1974 | Tourin |
| 3,826,249 A | 7/1974 | Lee et al. |
| 3,877,426 A | 4/1975 | Nirschl |
| 3,901,221 A | 8/1975 | Nicholson et al. |
| 3,920,006 A | 11/1975 | Lapidus |
| 4,013,069 A | 3/1977 | Hasty |
| 4,029,087 A | 6/1977 | Dye et al. |
| 4,030,488 A | 6/1977 | Hasty |
| 4,066,084 A | 1/1978 | Tillander |
| 4,091,804 A | 5/1978 | Hasty |
| 4,156,425 A | 5/1979 | Arkans |
| 4,198,961 A | 4/1980 | Arkans |
| 4,202,312 A | 5/1980 | Mori et al. |
| 4,202,325 A | 5/1980 | Villari et al. |
| 4,206,751 A | 6/1980 | Schneider |

(Continued)

FOREIGN PATENT DOCUMENTS

DE    19846922 A1    4/2000

(Continued)

OTHER PUBLICATIONS

PCT International Search Report, May 25, 2005, 4 pgs.
PCT International Search Report, Jun. 2, 2005, 5 pgs.

(Continued)

*Primary Examiner*—Quang D. Thanh
(74) *Attorney, Agent, or Firm*—Edward S. Jarmolowicz

(57) ABSTRACT

A compression apparatus including an expandable body configured for disposal about a foot. A strap extends from the body. The strap is configured for disposal about the foot adjacent an ankle. The strap has a first layer configured to engage an outer surface of the foot adjacent the ankle, a second layer and a third cushion layer disposed therebetween. The body may include a metatarsal portion. The first layer and the second layer may be configured to provide a barrier to the third cushion layer. The first layer may be configured to prevent engagement of the third cushion layer with the outer surface of the foot.

7 Claims, 6 Drawing Sheets

U.S. PATENT DOCUMENTS

| | | | |
|---|---|---|---|
| 4,207,875 | A | 6/1980 | Arkans |
| 4,207,876 | A | 6/1980 | Annis |
| 4,253,449 | A | 3/1981 | Arkans et al. |
| 4,280,485 | A | 7/1981 | Arkans |
| 4,320,746 | A | 3/1982 | Arkans et al. |
| 4,355,632 | A | 10/1982 | Sandman |
| 4,375,217 | A | 3/1983 | Arkans |
| 4,408,599 | A | 10/1983 | Mummert |
| 4,442,834 | A | 4/1984 | Tucker et al. |
| 4,453,538 | A | 6/1984 | Whitney |
| 4,531,516 | A | 7/1985 | Poole et al. |
| 4,580,816 | A | 4/1986 | Campbell et al. |
| 4,597,384 | A | 7/1986 | Whitney |
| 4,614,179 | A | 9/1986 | Gardner et al. |
| 4,614,180 | A | 9/1986 | Gardner et al. |
| 4,624,248 | A | 11/1986 | Poole et al. |
| 4,696,289 | A | 9/1987 | Gardner et al. |
| 4,702,232 | A | 10/1987 | Gardner et al. |
| 4,721,101 | A | 1/1988 | Gardner et al. |
| 4,722,332 | A | 2/1988 | Saggers |
| 4,730,606 | A | 3/1988 | Leininger |
| 4,762,121 | A | 8/1988 | Shienfeld |
| 4,827,912 | A | 5/1989 | Carrington et al. |
| RE32,939 | E | 6/1989 | Gardner et al. |
| RE32,940 | E | 6/1989 | Gardner et al. |
| 4,841,956 | A | 6/1989 | Gardner et al. |
| D302,301 | S | 7/1989 | Robinette-Lehman |
| 4,883,073 | A | 11/1989 | Aziz |
| 4,938,208 | A | 7/1990 | Dye |
| 5,007,411 | A | 4/1991 | Dye |
| 5,014,681 | A | 5/1991 | Neeman et al. |
| 5,022,387 | A | 6/1991 | Hasty |
| 5,031,604 | A | 7/1991 | Dye |
| 5,062,414 | A | 11/1991 | Grim |
| 5,186,163 | A | 2/1993 | Dye |
| 5,230,335 | A | 7/1993 | Johnson, Jr. et al. |
| 5,263,473 | A | 11/1993 | McWhorter |
| 5,277,695 | A | 1/1994 | Johnson, Jr. et al. |
| 5,314,455 | A | 5/1994 | Johnson, Jr. et al. |
| 5,354,260 | A | 10/1994 | Cook |
| 5,383,894 | A | 1/1995 | Dye |
| 5,389,065 | A | 2/1995 | Johnson, Jr. |
| D358,216 | S | 5/1995 | Dye |
| 5,413,142 | A | 5/1995 | Johnson et al. |
| 5,435,009 | A | 7/1995 | Schild et al. |
| 5,437,610 | A | 8/1995 | Cariapa et al. |
| 5,441,533 | A | 8/1995 | Johnson et al. |
| 5,466,250 | A | 11/1995 | Johnson, Jr. et al. |
| 5,478,119 | A | 12/1995 | Dye |
| 5,489,252 | A | 2/1996 | May |
| 5,489,259 | A | 2/1996 | Jacobs et al. |
| 5,496,262 | A | 3/1996 | Johnson, Jr. et al. |
| 5,514,081 | A | 5/1996 | Mann |
| D376,013 | S | 11/1996 | Sandman et al. |
| 5,575,762 | A | 11/1996 | Peeler et al. |
| 5,584,798 | A | 12/1996 | Fox |
| 5,588,955 | A | 12/1996 | Johnson, Jr. et al. |
| 5,591,200 | A | 1/1997 | Cone et al. |
| 5,626,556 | A | 5/1997 | Tobler et al. |
| 5,634,889 | A | 6/1997 | Gardner et al. |
| 5,653,244 | A | 8/1997 | Shaw |
| 5,669,872 | A | 9/1997 | Fox |
| 5,674,262 | A | 10/1997 | Tumey |
| 5,676,641 | A * | 10/1997 | Arensdorf et al. ............ 602/27 |
| 5,711,757 | A | 1/1998 | Bryant |
| 5,795,312 | A | 8/1998 | Dye |
| 5,840,049 | A | 11/1998 | Tumey et al. |
| 5,843,007 | A | 12/1998 | McEwen et al. |
| 5,876,359 | A | 3/1999 | Bock et al. |
| D411,301 | S | 6/1999 | Hampson et al. |
| 5,931,797 | A | 8/1999 | Tumey et al. |
| 5,951,502 | A | 9/1999 | Peeler et al. |
| 5,988,704 | A | 11/1999 | Ryhman |
| 5,989,204 | A | 11/1999 | Lina |
| 5,991,654 | A | 11/1999 | Tumey et al. |
| 5,997,495 | A | 12/1999 | Cook et al. |
| 6,001,119 | A | 12/1999 | Hampson et al. |
| 6,007,559 | A | 12/1999 | Arkans |
| 6,062,244 | A | 5/2000 | Arkans |
| 6,129,688 | A | 10/2000 | Arkans |
| 6,135,116 | A | 10/2000 | Vogel et al. |
| 6,152,495 | A | 11/2000 | Hoffmann et al. |
| 6,152,893 | A | 11/2000 | Pigg et al. |
| 6,231,532 | B1 | 5/2001 | Watson et al. |
| 6,257,626 | B1 | 7/2001 | Campau |
| 6,257,627 | B1 | 7/2001 | Fujiwara et al. |
| 6,290,662 | B1 | 9/2001 | Morris et al. |
| 6,296,617 | B1 | 10/2001 | Peeler et al. |
| 6,315,745 | B1 | 11/2001 | Kloecker |
| 6,319,215 | B1 | 11/2001 | Manor et al. |
| 6,322,530 | B1 | 11/2001 | Johnson, Jr. et al. |
| 6,358,219 | B1 | 3/2002 | Arkans |
| 6,368,357 | B1 | 4/2002 | Schon et al. |
| 6,387,065 | B1 | 5/2002 | Tumey |
| 4,721,101 | C1 | 6/2002 | Gardner et al. |
| 6,421,859 | B1 | 7/2002 | Hicks et al. |
| 6,423,053 | B1 | 7/2002 | Lee |
| 6,436,064 | B1 | 8/2002 | Kloecker |
| 6,440,093 | B1 | 8/2002 | McEwen et al. |
| 4,696,289 | C1 | 9/2002 | Gardner et al. |
| 6,447,460 | B1 | 9/2002 | Zheng et al. |
| 6,447,467 | B1 | 9/2002 | Barak |
| 6,463,934 | B1 | 10/2002 | Johnson, Jr. et al. |
| 6,468,237 | B1 | 10/2002 | Lina |
| 6,478,757 | B1 | 11/2002 | Barak |
| 6,488,643 | B1 | 12/2002 | Tumey et al. |
| 6,493,568 | B1 | 12/2002 | Bell et al. |
| 6,494,852 | B1 | 12/2002 | Barak et al. |
| 6,544,202 | B2 | 4/2003 | McEwen et al. |
| 6,557,704 | B1 | 5/2003 | Randolph |
| 6,589,534 | B1 | 7/2003 | Shaul et al. |
| 6,592,534 | B1 | 7/2003 | Rutt et al. |
| 6,629,941 | B1 | 10/2003 | Ishibashi et al. |
| 6,945,944 | B2 | 9/2005 | Kulper et al. |
| 2002/0042583 | A1 | 4/2002 | Barak et al. |
| 2002/0133106 | A1 | 9/2002 | Peled |
| 2003/0139696 | A1 | 7/2003 | Boukanov et al. |
| 2006/0020236 | A1 | 1/2006 | Ben-Nun |

FOREIGN PATENT DOCUMENTS

| | | | |
|---|---|---|---|
| EP | 0552515 | A1 | 7/1993 |
| EP | 0861651 | A1 | 9/1998 |
| EP | 1018329 | A2 | 7/2000 |
| GB | 2313784 | A | 12/1997 |
| WO | WO 99/63892 | | 12/1999 |
| WO | WO 2004/011842 | A1 | 2/2004 |

OTHER PUBLICATIONS

PCT International Search Report, Jun. 2, 2005, 7 pgs.
PCT Invitation to Pay Additional Fees, Jun. 10, 2005, 6 pgs.
The Kendall Company, Vascular Therapy Products Catalog, Jan. 1996, pp. 8-5-8-7.
The Kendall Company, The New SCD Compression Sleeve, Aug. 1993, pp. 1-2.
Tyco Healthcare Kendall, Prevention Gets Personal, Mar. 2001, pp. 1, 2, 4.
Kendall SCD, Sequential Compression Sleeves, Patent Information, Jan. 1993, 6 pgs.
Tyco Healthcare Kendall, SCD Soft Sleeve Catalog, Apr. 2001, pp. 1-2.
Tyco Healthcare Kendall, SCD Response Catalog, Mar. 2000, pp. 1-2.

* cited by examiner

COMPRESSION APPARATUS

BACKGROUND

1. Technical Field

The present disclosure generally relates to the field of vascular therapy for application to a limb of a body, and more particularly, to a compression apparatus configured to artificially stimulate blood vessels of the limb.

2. Description of the Related Art

A major concern for immobile patients and persons alike are medical conditions that form clots in the blood, such as, deep vein thrombosis (DVT) and peripheral edema. Such patients and persons include those undergoing surgery, anesthesia and extended periods of bed rest. These blood clotting conditions generally occur in the deep veins of the lower extremities and/or pelvis. These veins, such as the iliac, femoral, popiteal and tibial return deoxygenated to the heart. For example, when blood circulation in these veins is retarded due to illness, injury or inactivity, there is a tendency for blood to accumulate or pool. A static pool of blood is ideal for clot formations. A major risk associated with this condition is interference with cardiovascular circulation. Most seriously, a fragment of the blood clot can break loose and migrate. A pulmonary emboli can form blocking a main pulmonary artery, which may be life threatening.

The conditions and resulting risks associated with patient immobility may be controlled or alleviated by applying intermittent pressure to a patient's limb, such as, for example, portions of a leg and foot to assist in blood circulation. Known devices have been employed to assist in blood circulation, such as, one piece pads and compression boots. See, for example, U.S. Pat. Nos. 4,696,289 and 5,989,204.

Compression devices that consist of an air pump connected to a disposable wraparound pad by one or more air tubes have been used. The wraparound pad is placed around the patient's foot or other extremity. Air is then forced into the wraparound pad creating pressure around the parts of the foot or other extremity.

These known devices may suffer from various drawbacks due to their bulk, cumbersome nature of use, potential for contamination and irritation to the extremity during application and use. These drawbacks reduce comfort, compliance, cause skin breakdown and may disadvantageously prevent mobility of the patient as recovery progresses after surgery.

Therefore, it would be desirable to overcome the disadvantages and drawbacks of the prior art with a foot sleeve that prevents contamination, mitigates the incidence of skin breakdown and facilitates disposal with an extremity. It is contemplated that a compression apparatus including the foot sleeve reduces bulk and is not cumbersome during use to improve comfort and compliance to a patient. It is further contemplated that the compression apparatus is easily and efficiently manufactured.

SUMMARY

Accordingly, a compression apparatus is provided that prevents contamination, mitigates the incidence of skin breakdown and facilitates disposal with an extremity for overcoming the disadvantages and drawbacks of the prior art. Desirably, a compression apparatus including the foot sleeve reduces bulk and is not cumbersome during use to improve comfort and compliance to a patient. The compression apparatus is easily and efficiently fabricated.

The embodiments of the compression apparatus, according to the present disclosure, are configured to provide vascular therapy, including for example the prevention of deep vein thrombosis ("DVT") by artificially stimulating blood vessels throughout the foot of a patient, including the toes and the heel, to increase blood circulation for patients. The compression apparatus according to the present disclosure is an intermittent pneumatic compression device for applying slow compression to a foot. Such pressure simulates blood flow that would normally result from, for example, walking, by employing a foot sleeve that is supported about a foot of a patient.

The compression apparatus may have an inflatable bladder designed to cover and engage the entire area of the bottom of the foot, beyond the heel and ball to a substantial portion of the toes. The inflatable bladder wraps about the side portions of the foot via a hook and loop type connector flap that transverses the instep of the foot.

The inflatable bladder may include an outside layer and an inside layer. The bladder can be formed by welding the outside layer and the inside layer together. The bladder provides a uniform application of pressure to the entire foot and is then deflated. Moreover, the compression apparatus may include bladder sections that are capable of enabling venous refill detection. The compression apparatus according to the present disclosure includes various embodiments and combinations as will be appreciated herein. The various embodiments and combinations may each be manufactured in various sizes to accommodate subjects of varying sizes as well as right and left foot models.

The compression apparatus includes a strap that improves comfort by using a single piece laminate structure whose inside layer is a cushioning layer. The strap is integrated with a foot sleeve by sandwiching the strap between separate layers of the foot sleeve body. The comfort to the patient may be improved by segmenting the strap to contour about the heel of the foot. The strap can also include one or more layers configured to provide a barrier to the cushioning layer from the environment. The foot sleeve can improve ease of use by having a universal design with a one flap metatarsal closure.

The strap may include a laminate consisting of various layers. The layers may include a center layer that is configured for comfort. Outside layers disposed about the center layer provide a barrier between the environment and an outer surface of the foot. One of the outside layers can be a skin contact layer that is soft to the touch. The strap may be a separate part integrated into the body of the foot sleeve by being sandwiched between separate layers of the foot sleeve body and then permanently secured. The body of the foot sleeve may be designed for adaptability to various foot sizes and shapes by employing a single metatarsal flap that facilitates ease of use. The body may be configured to provide inspection of the tops of the phalanges of the foot.

One of the advantages of the present disclosure is a cushioning layer that is not in direct engagement with the outer surface of the foot. The cushioning layer has a soft skin contact layer. The foot sleeve may also include a liner that is configured to provide a physical barrier to the cushioning layer that assists in the prevention of contamination. The interior cushioning layer provides comfort and mitigates skin breakdown. Thus, the foot sleeve improves patient compliance and provides sanitation by isolating the cushioning layer from the environment.

The foot sleeve is also easily manufactured, for instance, the material stack up contained in the layers allows the strap and/or foot sleeve to be cut as one piece and ensures an even stack up of materials.

In one embodiment, in accordance with the principles of the present disclosure, the compression apparatus includes an expandable body configured for disposal about a foot. A strap extends from the body. The strap is configured for disposal about the foot adjacent an ankle. The strap has a first layer configured to engage an outer surface of the foot adjacent the ankle, a second layer and a third cushion layer disposed therebetween.

The strap may be integrally connected to the expandable body. Alternatively, the strap may be monolithically formed with the expandable body. The expandable body can include a first, top layer and/or a second, bottom layer. Moreover, a portion of the strap member may be disposed between a top and bottom layer of the foot sleeve body. The strap may have a segmented configuration for contour with the foot. The third cushion layer can be disposed within the first layer and the second layer such that the first layer and the second layer are configured to provide a barrier to the third cushion layer. The body can include a metatarsal strap.

Alternatively, the first layer includes a soft polyester material. The first layer may include a soft polyester material and polyvinylchloride. The third cushion layer may include a foam material. The second layer can have an outer surface including a loop material disposed therewith. The second layer may include a polyvinylchloride material and an outer surface having a loop material disposed therewith. Alternatively, the second layer has an outer surface including a loop material such that the metatarsal strap includes hook elements that are engageable with the loop material to mount the compression apparatus with the foot. The body may include hook elements that are engageable with the loop material to mount the compression apparatus with the foot.

In an alternate embodiment, the compression apparatus has a foot sleeve including an inflatable body configured for disposal about a foot. The foot sleeve includes a metatarsal portion. A strap is integrally connected to the foot sleeve and extends therefrom. The strap is configured for disposal about the foot adjacent an ankle. The strap has a first layer configured to engage an outer surface of the foot adjacent the ankle, a second layer and a third cushion layer is disposed therebetween. The first layer and the second layer are configured to provide a barrier to the third cushion layer. The first layer may be configured to prevent engagement of the third cushion layer with the outer surface of the foot.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, which are described below.

DETAILED DESCRIPTION OF EXEMPLARY EMBODIMENTS

The exemplary embodiments of the compression apparatus including the foot sleeve and methods of operation disclosed are discussed in terms of vascular therapy including a compression apparatus for application to a foot or other limb of a body and more particularly in terms of a compression apparatus configured to artificially stimulate the blood vessels of the limb including the foot, heel and toes of a patient. It is contemplated that the compression apparatus may be employed for preventing and overcoming the risks associated with patient immobility. It is further contemplated that the compression apparatus alleviates the conditions arising from patient immobility to prevent for example, DVT, and peripheral edema. It is contemplated that the compression apparatus according to the present disclosure may be employed with various types of venous compression systems, including, but not limited to rapid inflation, slow compression, non-sequential and sequential compression apparatus. It is envisioned that the present disclosure, however, finds application with a wide variety of immobile conditions of persons and patients alike, such as, for example, those undergoing surgery, anesthesia, extended periods of bed rest, obesity, advanced age, malignancy, and prior thromboembolism.

In the discussion that follows, the term "subject" refers to a patient undergoing vascular therapy using the compression apparatus. The following discussion includes a description of the compression apparatus, followed by a description of an exemplary method of operating the compression apparatus in accordance with the principals of the present disclosure. Reference will now be made in detail to the exemplary embodiments and disclosure, which are illustrated with the accompanying figures.

Figure 1:
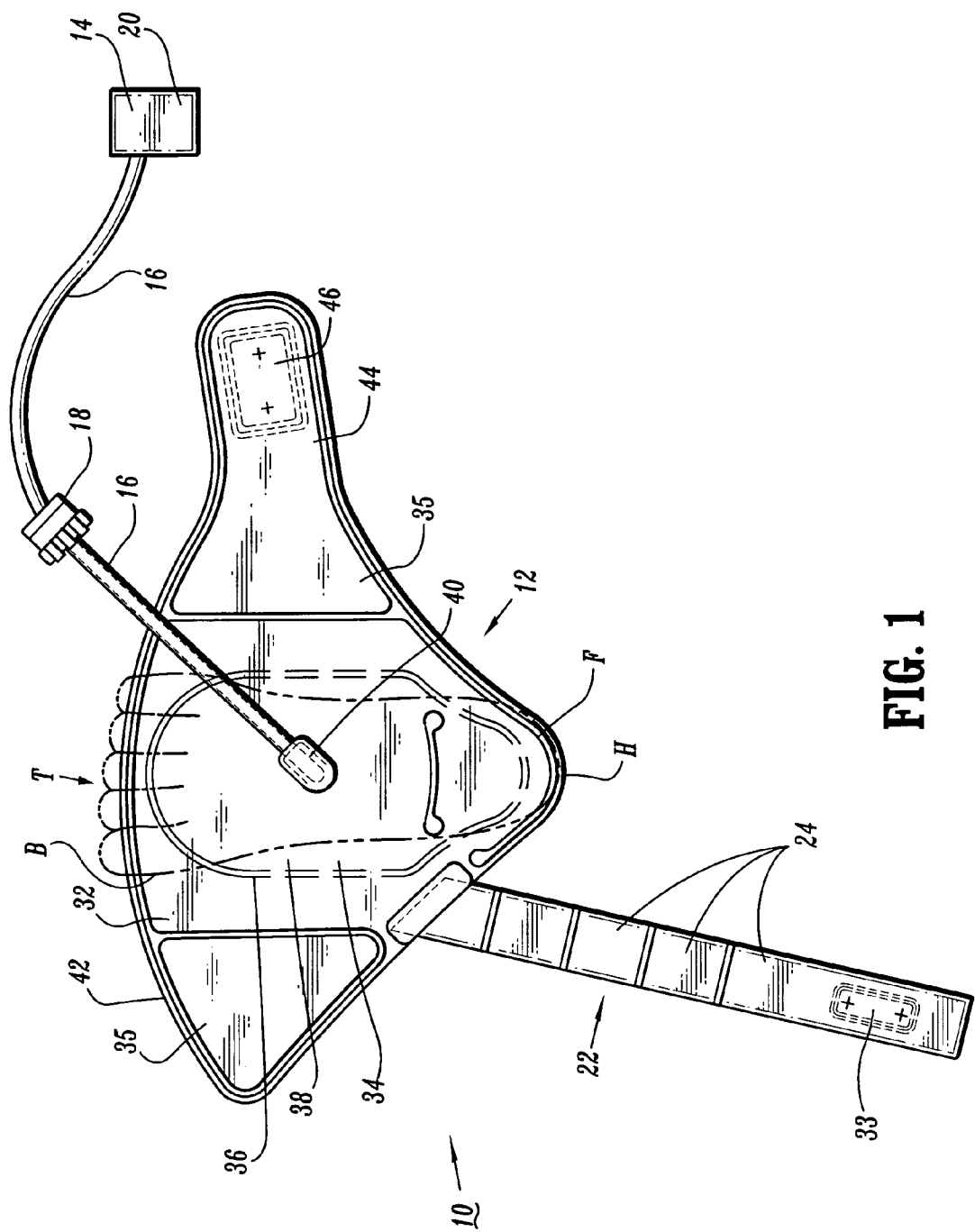
FIG. 1 is a plan view of one particular embodiment of a compression apparatus and showing an inflatable bladder and a foot in phantom, in accordance with the principles of the present disclosure.
Figure 1A:
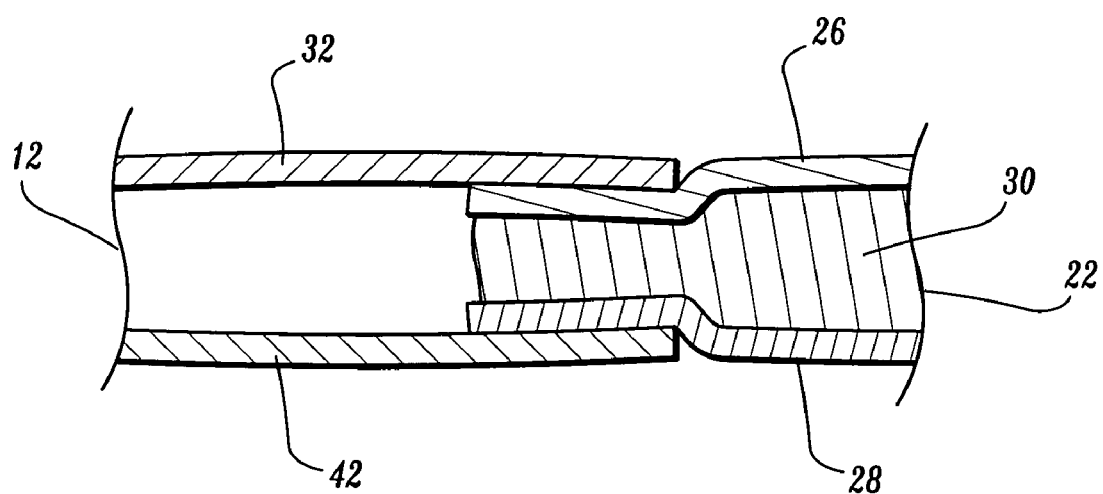
FIG. 1A is a partial cross-sectional view of the compression apparatus shown in FIG. 1.
Figure 2:
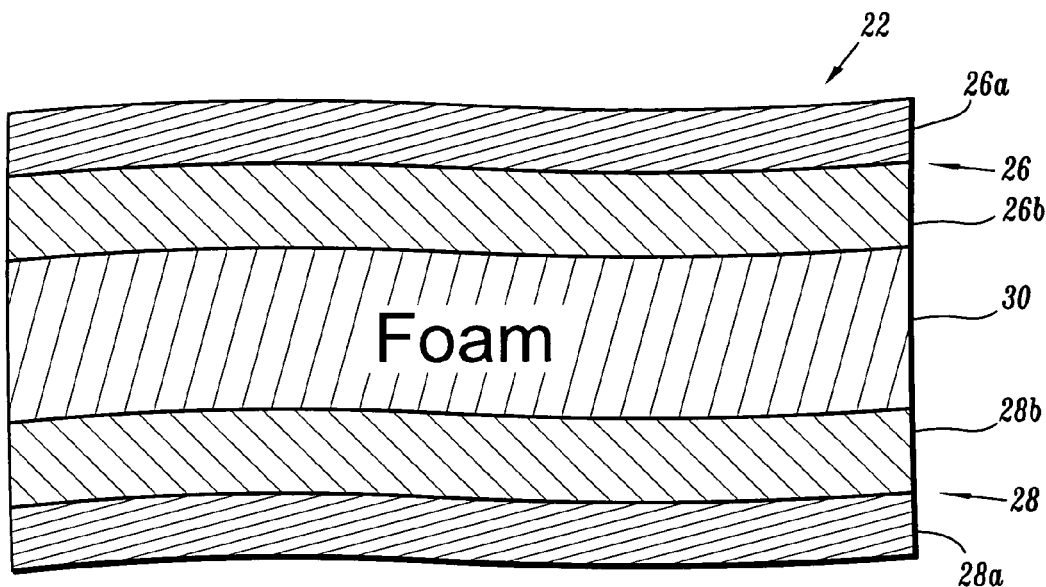
FIG. 2 is a cutaway cross section view of a strap of the compression apparatus shown in FIG. 1.

Turning now to the figures, wherein like components are designated by like reference numerals throughout the several views. Referring initially to FIGS. 1, 1A and 2, there is illustrated a compression apparatus 10, constructed in accordance with the principals of the present disclosure (see, for example, the compression sleeve described in U.S. patent application Ser. No. 10/784,607, filed on Feb. 23, 2004 and entitled Compression Apparatus, the entire contents of which is hereby incorporated by reference herein). Compression apparatus 10 includes an expandable body, such as, for example, a foot sleeve 12 configured for disposal about a foot F of a subject (not shown). Foot sleeve 12 may be disposed with the right or left foot of the subject. Foot sleeve 12 fluidly communicates with a pressurized fluid source 14 via tubing 16 and a valve connector 18 (see, for example, the valve connector described in U.S. patent application Ser. No.

10/784,639, filed on Feb. 23, 2004 and entitled Fluid Conduit Connector Apparatus, the entire contents of which is hereby incorporated by reference herein) for applying compression to the left foot and/or the right foot to provide vascular therapy to the subject and augment venous return. Compression apparatus 10 employs a controller 20 to regulate fluid pressure for vascular therapy. See, for example, the controller described in U.S. patent application Ser. No. 10/784,323, filed on Feb. 23, 2004 and entitled Compression Treatment System, the entire contents of which is hereby incorporated by reference herein. Pressurized fluid source 14 may include a pump and may be stationary or portable. It is contemplated that pressurized fluid source 14 may include the necessary electronics and computer software to carry out vascular therapy, in accordance with the principles of the present disclosure.

Foot sleeve 12 is configured to apply vascular therapy to the entire area of the bottom of foot F, beyond a heel H and a ball B to a substantial portion of toes T. It is contemplated that foot sleeve 12 and other parts of compression apparatus 10 may be disposed, wrapped and mounted with various limbs and extremities of a subject's body, such as, for example, legs and arms. It is further contemplated that foot sleeve 12 or portions thereof may be disposable. It is envisioned that foot sleeve 12 may include flexible sections, such as, elastic or spandex materials to facilitate mobility of a limb during use. The components of strap 22 may be fabricated from materials suitable for compression vascular therapy such as, for example, films and fabrics, such as PVC (polyvinyl chloride) and PE (polyethylene).

Strap 22 is configured for disposal about foot F adjacent to the ankle. Strap 22 is integrally connected to foot sleeve 12 and fixedly mounted between a foot contact layer 26 and an outer layer 28 of foot sleeve 12, as will be discussed. Strap 22 may be monolithically formed with foot sleeve 12, wherein at least a portion of the strap 22 is formed from the same contiguous material as a portion of the foot sleeve 12. By way of non-limiting example, foot contact layer 26 may be formed from the same contiguous material as foot contact layer 32 of foot sleeve 12. Strap 22 has segmented portions 24 that are configured to contour about heel H of foot F. It is contemplated that segmented portions 24 may be variously configured and dimensioned, such as, rounded or alternatively, strap 22 may have a uniform outer surface, such as, smooth.

Strap 22 has a first layer, such as, for example, foot contact layer 26 that is configured to engage to an outer surface of foot F adjacent the ankle. Foot contact layer 26 includes a soft polyester material 26a that is soft for engaging the skin of the subject. This soft skin contact layer 26 advantageously provides comfort to the subject, prevents contamination and mitigates skin breakdown. Foot contact layer 26 may also include a PVC portion 26b disposed adjacent soft polyester material 26a.

A second layer, such as, for example, outer layer 28 cooperates with foot contact layer 26 such that a third layer 30 is disposed therebetween. Third layer 30 includes a foam material to provide a cushioning effect to the subject. It is contemplated that layer 30 may include alternative materials that provide a cushioned configuration. Outer layer 28 includes a loop type material 28a disposed therewith, for engagement with a corresponding hook element of foot sleeve 12, and a PVC portion 28b disposed adjacent loop material 28a. Outer layer 28 advantageously prevents contamination of third cushion layer 30 from the environment, such as, for example, air, moisture and dirt.

Figure 3:
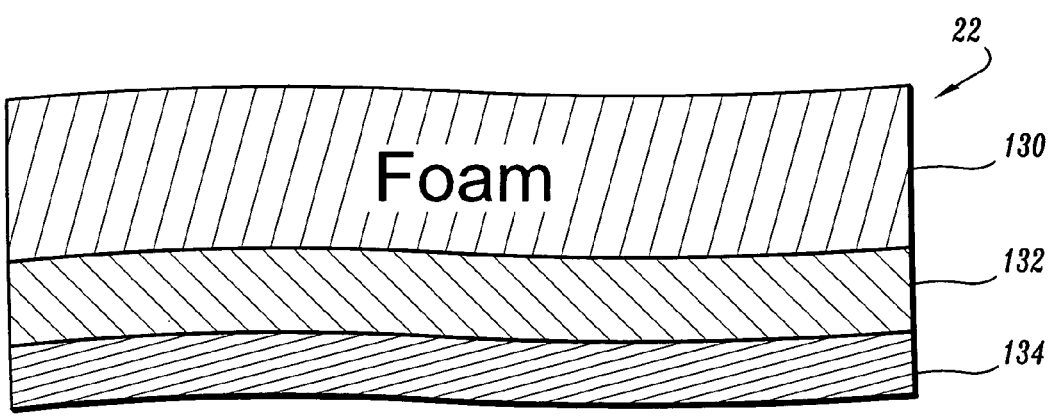
FIG. 3 is a cutaway cross section view of an alternate embodiment of the strap of the compression apparatus shown in FIG. 1.

Foot contact layer 26 and outer layer 28 are configured to form a physical barrier to third cushion layer 30. This configuration advantageously provides comfort to the subject, as well as compliance, and prevents contamination of third cushioning layer 30. In an alternate embodiment, as shown in FIG. 3, strap 22 includes a laminate structure having a cushion layer 130 and a PVC portion 132 disposed adjacent thereto. An outer layer 134 is disposed adjacent PVC portion 132. Layer 134 may include a soft polyester material for engaging the outer surface of foot F, or alternatively, may include a loop material to prevent contamination of cushion layer 130 from the environment.

Foot contact layer 26 and outer layer 28 are overlaid to form strap 22. Foot contact layer 26 and outer layer 28 are fixedly joined at seams adjacent corresponding perimeters thereof, to support the components of strap 22. The components of strap 22 may be bonded via welding, e.g., RF welding, adhesive, industrial strength double sided tape and the like. It is envisioned that only a portion of the foot contact layer 26 and outer layer 28 are joined. It is further envisioned that strap 22 includes a plurality of seams, disposed variously thereabout, that join foot contact layer 26 and outer layer 28.

In an alternative embodiment and with reference to FIG. 1A, an exaggerated partial cross-sectional view of a strap member 22 and its union to foot sleeve 12 is shown. The strap member 22 is disposed between the foot contact layer 32 and outer layer 42 of foot sleeve 12 such that the union of strap 22 and foot sleeve 12 is generally uniform. Such uniformity provides additional comfort to the user of the foot sleeve 12. More particularly, foot contact layer 26 and outer layer 28 of strap 22 are joined to interior portions of foot contact layer 32 and outer layer 42 of foot sleeve 12. Alternatively, it is also contemplated that cushioning layer 30 may or may not be disposed between foot contact layer 32 and outer layer 42 of foot sleeve 12.

Strap 22 has a longitudinally projecting configuration extending from foot sleeve 12 and is configured for disposal about portions of foot F adjacent the ankle. Strap 22 forms part of a hook and loop type connector. A hook element 33 is mounted to strap 22 at foot contact layer 26. As strap 22 is wrapped about the portions of foot F adjacent the ankle, hook element 33 engages the loop material of outer layer 42 of foot sleeve 12 to facilitate mounting of foot sleeve 12 with foot F. Alternative to hook and loop type elements, clips, adhesive and pins may be employed.

Foot sleeve 12 includes a foot contact layer 32 configured to engage foot F for applying pressure thereto. Foot contact layer 32 has sections 35 and is flexible for conforming to the shape of foot F. It is envisioned that foot contact layer 32 may be fabricated from a polyester fabric. It is contemplated that foot contact layer 32 may be configured for wicking fluids such as, moisture and perspiration from an outer surface of foot F. Foot contact layer 32 may be treated chemically to enhance such wicking effect. Alternatively, foot contact layer 32 may be monolithically formed with foot contact layer 26 of strap 22.

An inflatable bladder 34 of foot sleeve 12 includes an upper bladder layer 36 and a lower bladder layer 38 that are overlaid to form inflatable bladder 34. Upper bladder layer 36 engages foot contact layer 32 to facilitate application of pressure for vascular therapy to foot F. Upper bladder layer 36 and lower bladder layer 38 are fixedly joined via welding at seams along their perimeters to define inflatable bladder 34. It is contemplated that inflatable bladder 34 may include a plurality of seams, disposed variously thereabout, that join upper bladder layer 36 and lower bladder layer 38. It is further contemplated that the seams may be formed by adhesive, heat sealed and the like.

Upper bladder layer 36 and lower bladder layer 38 may be fabricated from a laminated material, for example, a PVC material. It is contemplated that each bladder layer may have a thickness of approximately 6-15 mils. It is further contemplated that the PVC material may be laminated to a non-woven or woven material and is RF heat sealable. Upper bladder layer 36 and lower bladder layer 38 may be fabricated from two different thicknesses to provide directional inflation. It is envisioned that the overall dimensions and materials described throughout this disclosure are not limiting and that other dimensions and materials may be used. It is further envisioned that inflatable bladder 34 may define one or a plurality of expandable chambers.

Inflatable bladder 34 extends along foot F to apply vascular therapy to the entire area of the bottom of foot F, beyond heel H and ball B to a substantial portion of toes T. It is contemplated that inflatable bladder 34 may have various geometric configurations, such as, circular, elliptical and rectangular. Inflatable bladder 34 includes an inlet port 40 that connects to tubing 16 to facilitate fluid communication with pressurized fluid source 14.

An outer layer 42 of foot sleeve 12 is disposed adjacent to lower bladder layer 38. Outer layer 42 may be fabricated from a laminated material including fabric and a loop material, for example, a loop/non-woven laminate. Outer layer 42 provides an attachment surface for hook elements. Alternatively, outer layer 42 may be monolithically formed with outer layer 28 of strap 22.

Outer layer 42 may include die cut holes to provide for a fluid inlet to pass through, such as inlet port 40. It is envisioned that outer layer 42 and other portions of foot sleeve 12 may include vent openings disposed variously thereabout to provide cooling to the subject and increase mobility during use.

Foot contact layer 32 and outer layer 42 are overlaid to form foot sleeve 12. Foot contact layer 32 and outer layer 42 are fixedly joined at seams adjacent corresponding perimeters thereof, to support the components of foot sleeve 12. The components of foot sleeve 12 may be bonded via welding, e.g., RF welding, adhesive, industrial strength double sided tape and the like. It is envisioned that only a portion of the perimeters of foot contact layer 32 and outer layer 42 are joined. It is envisioned that foot sleeve 12 includes a plurality of seams, disposed variously thereabout, that join foot contact layer 32 and outer layer 42.

The components of foot sleeve 12 may be fabricated from materials suitable for compression vascular therapy such as, for example, films and fabrics, such as PVC (polyvinyl chloride) and PE (polyethylene), depending on the particular vascular therapy application and/or preference. Semi-flexible and flexible fabrics, such as urethanes and silicones may also be used. Moreover, foot sleeve 12 may be fabricated from synthetic, natural, and non-woven materials of varying degrees of softness and pliability. One skilled in the art, however, will realize that other materials and fabrication methods suitable for assembly and manufacture, in accordance with the present disclosure, also would be appropriate.

Foot sleeve 12 is configured to support inflatable bladder 34. Foot sleeve 12 extends laterally and is configured for disposal about foot F and mounting thereto. Foot sleeve 12 is disposed with foot F such that the top portion of toes T are visible for observation and inspection. A metatarsal flap 44 of foot sleeve 12 wraps about the side portions of foot F and transverses the instep of foot F during vascular therapy. Metatarsal flap 44 forms part of a hook and loop type connector. A hook element 46 is mounted to foot sleeve 12 at foot contact layer 32. As metatarsal flap 44 is wrapped about foot F, hook element 46 engages the loop material of outer layer 42 to facilitate mounting of foot sleeve 12 with foot F. In turn, this causes inflatable bladder 34 to be disposed about foot F for vascular therapy. This configuration of foot sleeve 12 advantageously engages foot F to augment circulation of vessels of the limb. It is contemplated that foot sleeve 12 may have various geometric configurations, such as, circular, elliptical, and rectangular. Alternative to hook and loop type elements, clips, adhesive, and pins may be employed.

Compression apparatus 10, similar to that described above, is assembled and packaged for use. In operation, foot sleeve 12 of compression apparatus 10 is disposed about foot F and in fluid communication with pressurized fluid source 14, as discussed. Controller 20 regulates vascular therapy of compression apparatus 10 to a subject. Foot sleeve 12 applies compression to foot F to provide vascular therapy to the subject and augment venous return. It is envisioned that compression apparatus 10 may include inflatable sleeves for disposal about various portions of a subject's limb, such as for example, thigh, calf, ankle and that a second limb may be treated in alternate compression cycles with other sleeve(s).

For example, during a selected compression cycle for controller 20, inflatable bladder 34 is slowly inflated for 5 seconds with air to a pressure, such as 130 mm Hg. This configuration provides vascular therapy to foot F and augments venous return. At the end of the inflation and hold, foot sleeve 12 is vented and inflatable bladder 34 is deflated. Other compression cycles and pressures are also contemplated.

In an alternate embodiment, compression apparatus 10 performs venous refill time measurement. Venous refill time (VRT) measurement is an air plethysmographic technique that determines when the veins of a limb have completely refilled with blood following a compression cycle. See, for example, the venous refill time measurement described in U.S. Pat. No. 6,231,352 to Watson et al., the entire contents of which is hereby incorporated by reference herein. The VRT minimizes the amount of time that the blood remains stagnant inside the veins. The VRT is substituted for the default rest time between compression cycles. It is contemplated that the VRT technique and algorithm can be used for both leg sleeve and foot sleeve compression.

The VRT measurement uses an air plethysmographic technique where a low pressure is applied to inflatable bladder 34. As the veins fill with blood, the pressure in inflatable bladder 34 increases until a plateau is reached. The time that it takes for the pressure to plateau is the VRT. If two sleeves are connected to controller 20, then the VRT is determined separately for each limb being compressed and the greater of the two measurements is used as the new vent time of the compression cycle. The VRT measurement for each sleeve is made as each particular sleeve reaches set pressure independently. However, the vent time is not updated until VRT measurements have been calculated for both sleeves.

For example, compression apparatus 10 may employ the VRT measurement after the system initiates vascular therapy. Subsequently, after 30 minutes have elapsed, a VRT measurement will be taken on the next full inflation cycle. After foot sleeve 12 inflates, inflatable bladder 34 is vented down to zero.

It is contemplated that a selected bladder pressure is monitored and the vent to the bladder is closed when the pressure falls to 5-7 mm Hg. If the pressure in the bladder is 5-7 mm Hg on a current cycle then a VRT measurement is taken. If the pressure in the bladder does not vent down to 5-7 mm Hg then the vent time will remain at its current value and another measurement will be made in 30 minutes.

The VRT measurement algorithm determines when the pressure in inflatable bladder 34 plateaus after compression. The VRT measurement algorithm initiates with a time counter started from the end of the inflation cycle, which occurs after inflatable bladder 34 reaches 5-7 mm Hg (enough pressure to cause the bladder to remain in contact with the surface of the foot) and the venting is stopped. The VRT measurement initiates with the time counter started from the end of the inflation cycle.

The pressure in inflatable bladder 34 is then monitored with a 10-second, moving sample window. The window moves in 1-second intervals. When the difference between the first and last values in the window is less than approximately 0.05-0.5 mm Hg, the curve has reached its plateau. The VRT measurement is considered done, and the time interval is determined. The end of the window is considered to be the point at which the venous system in the foot has refilled.

The VRT measurement is considered erroneous if at any time during the measurement, the pressure in inflatable bladder 34 is below 2 mmHg, the calculation is discarded, and the old value of VRT is used. This may occur if there is a leak in the system. It is contemplated that if the pressure is greater than 20 mmHg at any time during the VRT measurement, the old value of the VRT is used.

Figure 4:
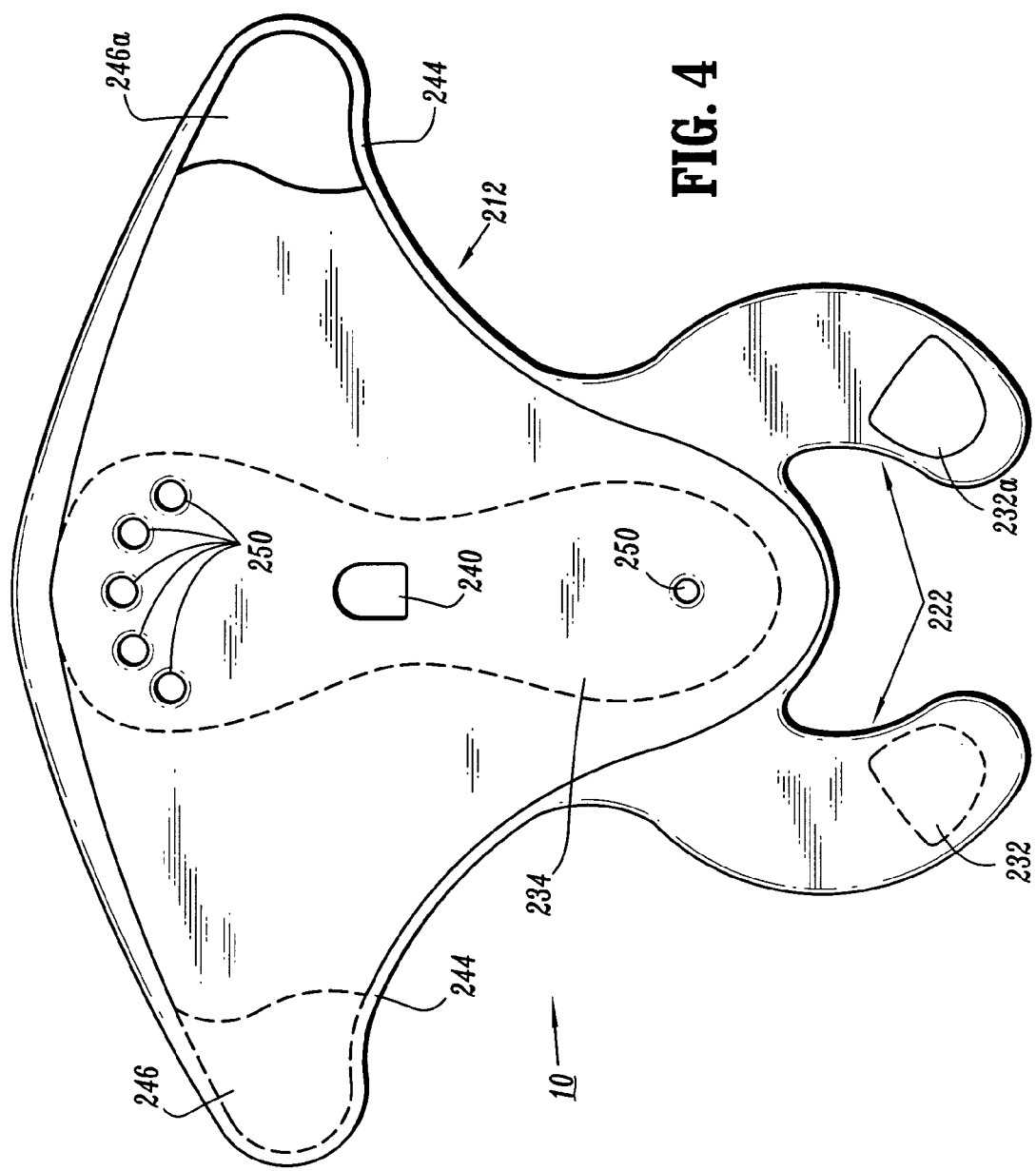
FIG. 4 is a plan view of an alternate embodiment of the compression apparatus shown in FIG. 1, illustrating an inflatable bladder in phantom.

Referring to FIG. 4, an alternate embodiment of compression apparatus 10 is shown. Compression apparatus 10 includes a foot sleeve 212, similar to foot sleeve 12 described above with regard to FIGS. 1, 1A and 2, configured for disposal about foot F. A pair of straps 222, similar to strap 22 described above with regard to FIGS. 1, 1A and 2, extend from foot sleeve 212. Straps 222 are configured for disposal about foot F adjacent to the ankle. One or a plurality of straps 222 may be employed.

Straps 222 have a longitudinally projecting configuration extending from foot sleeve 212 and are configured for disposal about portions of foot F adjacent the ankle. As discussed herein, it is contemplated that straps 222 may be separately or monolithically formed with foot sleeve 212. Straps 222 form part of hook and loop type connectors. Hook element 232 and loop element 232a are mounted to straps 222. As each of straps 222 are wrapped about the portions of foot F adjacent the ankle, hook element 232 engages loop material 232a to facilitate mounting of foot sleeve 212 with foot F. It is contemplated that hook elements 232, 232a may engage loop material disposed with an outer surface of foot sleeve 212 to facilitate mounting of foot sleeve 212 with foot F.

An inflatable bladder 234, similar to bladder 34 described above with regard to FIGS. 1 and 2, extends longitudinally along foot F to apply vascular therapy to the entire area of the bottom of foot F, beyond heel H and ball B to a substantial portion of toes T. Inflatable bladder 234 includes an inlet port 240 that connects to tubing 16 to facilitate fluid communication with pressurized fluid source 14.

Foot sleeve 212 is configured to support inflatable bladder 234. Foot sleeve 212 extends laterally and is configured for disposal about foot F and mounting thereto. Foot sleeve 212 is disposed with foot F such that the top portion of toes T are visible for observation and inspection. A pair of metatarsal flaps 244 extend laterally from foot sleeve 212 for wrapping about the side portions of foot F and transversing the instep of foot F during vascular therapy. Metatarsal flaps 244 form the hook and loop type connectors. Hook element 246 and loop element 246a are mounted to foot sleeve 212. As metatarsal flaps 244 are wrapped about foot F, hook element 246 engages to loop element 246a to engage the foot sleeve 212 to facilitate mounting of foot sleeve 212 with foot F. In turn, this causes inflatable bladder 234 to be disposed about foot F for vascular therapy. This configuration of foot sleeve 212 advantageously engages foot F to augment circulation of vessels of the limb. Foot sleeve 212 includes vent openings 250 disposed to provide cooling to the subject and increase mobility during use.

Figure 5:
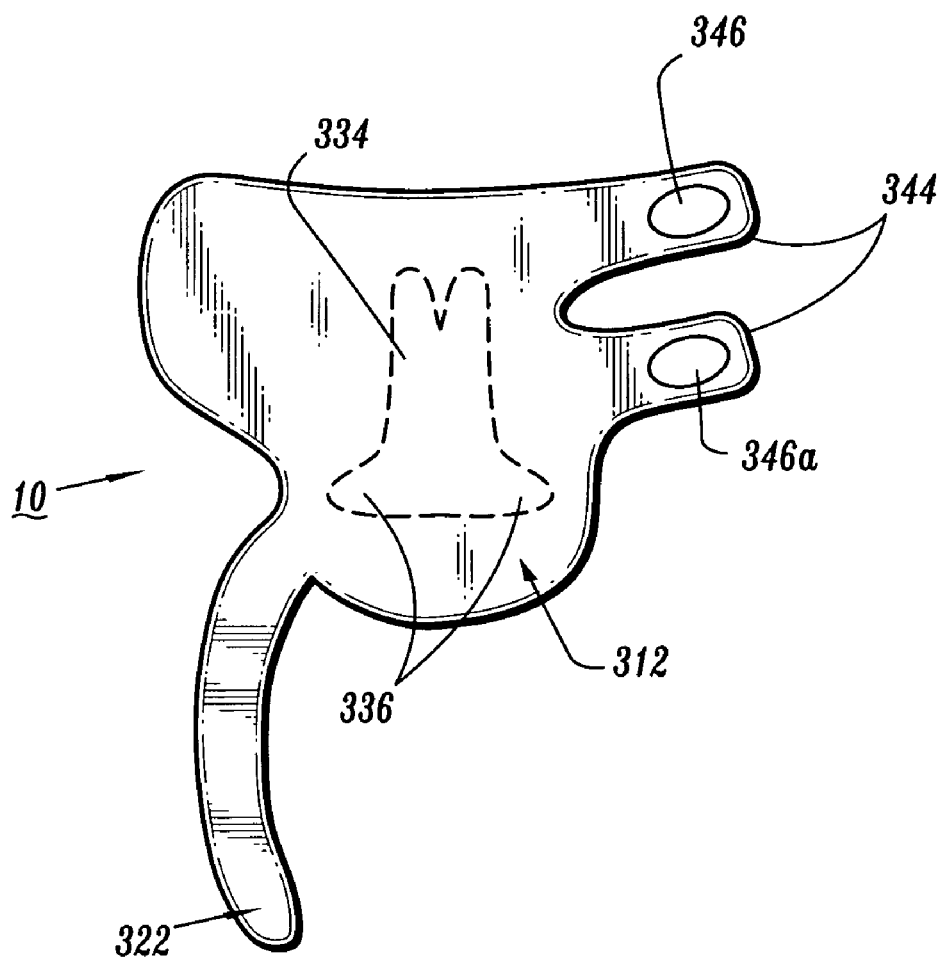
FIG. 5 is a plan view of another alternate embodiment of the compression apparatus shown in FIG. 1, illustrating an inflatable bladder in phantom.

Referring to FIG. 5, another alternate embodiment of compression apparatus 10 is shown. Compression apparatus 10 includes a foot sleeve 312, similar to those described above, configured for disposal about foot F. A strap 322, similar to those described above, extends from foot sleeve 312. An inflatable bladder 334, similar to those described above, extends longitudinally along foot F to apply vascular therapy to the entire area of the bottom of foot F, beyond heel H and ball B to a substantial portion of toes T. Inflatable bladder 334 includes side portions 336 that extend laterally therefrom to engage side portions of foot F during application of foot sleeve 312 with foot F.

Foot sleeve 312 is configured to support inflatable bladder 334. Foot sleeve 312 extends laterally and is configured for disposal about foot F and mounting thereto. Foot sleeve 312 is disposed with foot F such that the top portion of toes T are visible for observation and inspection. A pair of metatarsal flaps 344 extend laterally from one side of foot sleeve 312 for wrapping about the side portions of foot F and transversing the instep of foot F during vascular therapy. Metatarsal flaps 344 form part of hook and loop type connectors. Hook elements 346, 346a are mounted to foot sleeve 312. As metatarsal flaps 344 are wrapped about foot F, hook elements 346, 346a engage the loop material of foot sleeve 312 to facilitate mounting of foot sleeve 312 with foot F. In turn, this causes inflatable bladder 334 to be disposed about foot F, including side portions 336 engaging the side portions of foot F, for vascular therapy. This configuration of foot sleeve 312 advantageously engages foot F to augment circulation of vessels of the limb.

Figure 6:
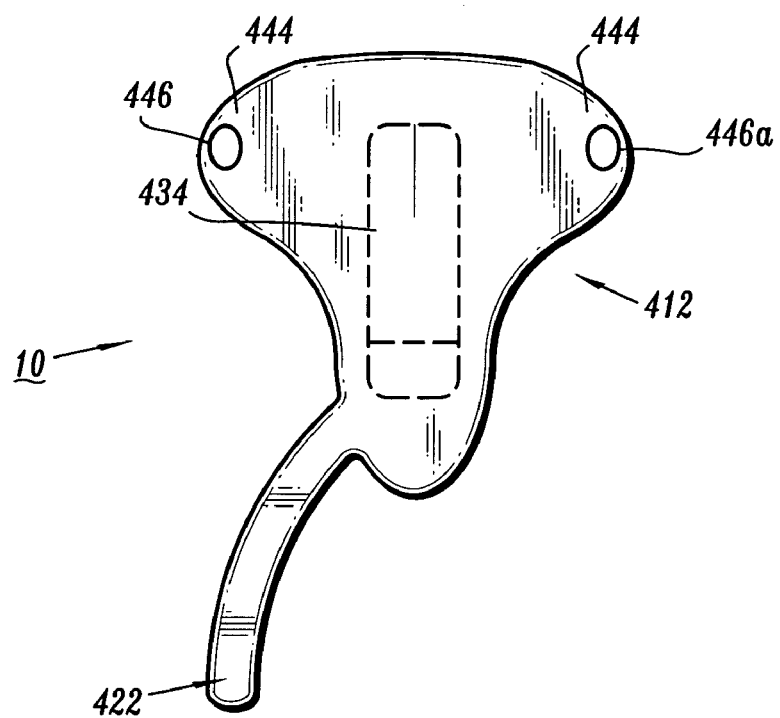
FIG. 6 is a plan view of another alternate embodiment of the compression apparatus shown in FIG. 1, illustrating an inflatable bladder in phantom.

Referring to FIG. 6, another alternate embodiment of compression apparatus 10 is shown. Compression apparatus 10 includes a foot sleeve 412, similar to those described above, configured for disposal about foot F. A strap 422, similar to those described above, extends from foot sleeve 412. An inflatable bladder 434, similar to those described above, extends longitudinally along foot F to apply vascular therapy to the bottom of foot F, beyond heel H and ball B to a substantial portion of toes T.

Foot sleeve 412 has wings 444 (similar to metatarsal flaps described above) and is configured to support inflatable bladder 434. Foot sleeve 412 extends laterally, via wings 444, and is configured for disposal about foot F and mounting thereto. Foot sleeve 412 is disposed with foot F such that the top portion of toes T are visible for observation and inspection. Wings 444 wrap about the side portions of foot F and transverse the instep of foot F during vascular therapy. Wings 444 form part of hook and loop type connectors. Hook element 446 and loop element 446a are mounted to wings 444. As wings 444 are wrapped about foot F, hook element 446 engages with loop element 446a to facilitate mounting of foot sleeve 412 with foot F. In turn, this causes inflatable bladder 434 to be disposed about foot F for vascular therapy. This configuration of foot sleeve 412 advantageously engages foot F to augment circulation of vessels of the limb.

Figure 7:
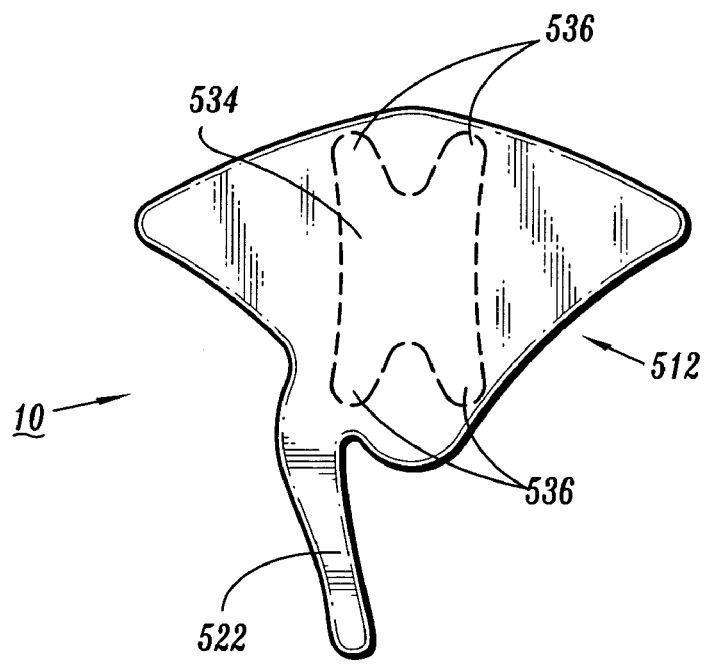
FIG. 7 is a plan view of another alternate embodiment of the compression apparatus shown in FIG. 1, illustrating an inflatable bladder in phantom.

Referring to FIG. 7, another alternate embodiment of compression apparatus 10 is shown. Compression apparatus 10 includes a foot sleeve 512, similar to those described above, configured for disposal about foot F. A strap 522, similar to those described above, extends from foot sleeve 512. An inflatable bladder 534, similar to those described above, extends longitudinally along foot F to apply vascular therapy to the bottom of foot F, beyond heel H and ball B to a substantial portion of toes T. Inflatable bladder 534 includes longitudinal portions 536 that extend longitudinally therefrom to engage desired portions of the bottom of foot F during application of foot sleeve 512 with foot F. Foot sleeve 512 is configured to support inflatable bladder 534. This configuration of foot sleeve 512 advantageously engages foot F to augment circulation of vessels of the limb.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A compression apparatus comprising:
   a foot sleeve including an inflatable body configured for disposal about a foot, the foot sleeve including a metatarsal portion;
   the foot sleeve further having a contact layer and an outer layer, the layers fixedly joined at a perimeter of the foot sleeve defining a first piece;
   a heel strap comprising a first layer and a second layer fixedly joined at a perimeter of the first and second layer, and a third layer between the first and second layer and the three layers defining a second piece; and
   wherein a portion of the second piece is received within the first piece between the contact layer and outer layer at the perimeter of the first piece, and the second piece is fixedly joined at the perimeter of the first piece, the second piece projects out through the sealed first piece at its perimeter and extends a substantial length outwardly therefrom for wrapping over and around the foot adjacent an ankle of a patient.

2. A compression apparatus as recited in claim 1, wherein the first layer and second layer of the second piece is fixedly joined at the perimeter of the first and second layer for sealing the third layer.

3. A compression apparatus as recited in claim 1, wherein the third layer includes a foam material for cushion during patient use.

4. A compression apparatus as recited in claim 1, wherein the second piece has at least one segmented portion configured for contour with the foot.

5. A compression apparatus as recited in claim 1, wherein the first layer of the strap having an outer surface that includes a loop material such that the metatarsal portion includes hook elements that are engageable with the loop material on the second piece to mount the foot sleeve with the foot.

6. A compression apparatus as recited in claim 1, wherein the compression apparatus includes a plurality of second pieces extending from the foot sleeve.

7. A compression apparatus as recited in claim 1, wherein the second piece includes a plurality of layers, whereby the plurality of layers comprises an interiorly disposed cushion layer.

* * * * *